United States Patent [19]

Rembaum et al.

[11] 4,438,239

[45] Mar. 20, 1984

[54] MICROSPHERE COATED SUBSTRATE CONTAINING REACTIVE ALDEHYDE GROUPS

[75] Inventors: Alan Rembaum, Pasadena; Richard C. K. Yen, Glendale, both of Calif.

[73] Assignee: California Institute of Technology, Pasadena, Calif.

[21] Appl. No.: 248,898

[22] Filed: Mar. 30, 1981

[51] Int. Cl.³ .................. C07G 7/00; C12N 11/08; B05D 3/06; C08F 16/34

[52] U.S. Cl. ........................... 525/54.1; 424/33; 424/94; 424/177; 204/159.21; 427/36; 428/327; 428/407; 435/7; 435/180; 526/315

[58] Field of Search ............... 435/7, 174, 180, 182, 435/176; 204/159.21, 158 HE; 428/327, 407; 427/36; 525/54.1; 526/315; 424/33, 94, 177; 260/29.7 M, 8, 112 R

[56] References Cited

U.S. PATENT DOCUMENTS

| | | | |
|---|---|---|---|
| 3,105,801 | 10/1963 | Bell et al. | 526/315 X |
| 3,849,253 | 11/1974 | Harvey et al. | 435/182 |
| 3,957,741 | 5/1976 | Rembaum et al. | 204/159.22 X |
| 4,035,316 | 7/1977 | Yen et al. | 260/8 X |
| 4,048,018 | 9/1977 | Coughlin et al. | 435/176 X |
| 4,070,348 | 1/1978 | Kraemer et al. | 435/180 X |
| 4,138,383 | 2/1979 | Rembaum et al. | 260/8 X |
| 4,141,857 | 2/1979 | Levy et al. | 435/180 X |
| 4,157,323 | 6/1979 | Yen et al. | 260/29.7 M |
| 4,193,910 | 3/1980 | Rohrbach et al. | 435/180 X |
| 4,239,646 | 12/1980 | Vincent et al. | 428/327 X |
| 4,267,234 | 5/1981 | Rembaum | 428/407 X |
| 4,267,235 | 5/1981 | Rembaum et al. | 428/407 |

*Primary Examiner*—David M. Naff
*Attorney, Agent, or Firm*—Marvin E. Jacobs

[57] ABSTRACT

A synthetic organic resin is coated with a continuous layer of contiguous, tangential, individual microspheres having a uniform diameter preferably between 100 Angstroms and 2000 Angstroms. The microspheres are an addition polymerized polymer of an unsaturated aldehyde containing 4 to 20 carbon atoms and are covalently bonded to the substrate by means of high energy radiation grafting. The microspheres contain reactive aldehyde groups and can form conjugates with proteins such as enzymes or other aldehyde reactive materials.

9 Claims, 3 Drawing Figures

MICROSPHERE COATED SUBSTRATE CONTAINING REACTIVE ALDEHYDE GROUPS

DESCRIPTION

Origin of the Invention

The invention described herein was made in the performance of work under a NASA contract and is subject to the provisions of Section 305 of the National Aeronautics and Space Act of 1958, Public Law 83-568 (72 Stat. 435; 43 USC 2457).

TECHNICAL FIELD

The present invention relates to the synthesis of polyacrolein coated substrate, functional derivatives thereof, fluoroescent and magnetic variations thereof, protein conjugates thereof and to the use of the coated substrate in biological and chemical research and analysis, as separation media for proteins or metals or as a substrate support for metal catalysts or enzymes.

BACKGROUND OF THE PRIOR ART

The isolation and characterization of cell membranes and their components is essential for an understanding of the role in which surface membranes play in regulating a wide variety of biological and immunological activities. The present techniques used for this purpose are not quite satisfactory.

Knowledge of the nature, number and distribution of specific receptors on cell surfaces is of central importance for an understanding of the molecular basis underlying such biological phenomena as cell-cell recognition in development, cell communication and regulation by hormones and chemical transmitters, and differences in normal and tumor cell surfaces. In previous studies, the localization of antigens and carbohydrate residues on the surface of cells, notably red blood cells and lymphocytes, has been determined by bonding antibodies or lectins to such molecules as ferritin, hemocyanin or peroxidase which have served as markers for transmission electron microscopy. With advances in high resolution scanning electron microscopy (SEM), however, the topographical distribution of molecular receptors on the surfaces of cell and tissue specimens can be readily determined by similar histochemical techniques using newly developed markers resolvable by SEM.

Recently, commercially available polystyrene latex particles have been utilized as immunologic markers for use in the SEM technique. The surface of such polystyrene particles is hydrophobic and hence certain types of macromolecules such as antibodies are absorbed on the surface under carefully controlled conditions. However, such particles stick non-specifically to many surfaces and molecules and this seriously limits their broad application.

The preparation of small, stable spherical Poly-Hema particles which are biocompatible, i.e., do not interact non-specifically with cells or other biological components and which contain functional groups to which specific proteins and other biochemical molecules can be covalently bonded is disclosed in U.S. Pat. No. 3,957,741.

Smaller, more evenly shaped acrylic microspheres are disclosed in U.S. Pat. No. 4,138,383. Microspheres having a density differing from that of cell membranes are disclosed in U.S. Pat. No. 4,035,316 and fluorescentacrylic copolymer microspheres are disclosed in Ser. No. 718,104 filed Aug. 27, 1976.

The hydroxyl groups can be activated by cyanogen bromide for covalent bonding of proteins and other chemicals containing amino groups to the polymeric bead. Methacrylic acid residues which impart a negative charge onto the particles are likely to prevent non-specific binding to cell surfaces and to provide carboxyl groups to which a variety of biochemical molecules can be covalently bonded using the carbodiimide method.

The derivatization procedure is unnecessarily complex and requires an additional step to prepare the bead surface for covalently binding to proteins such as antibodies, lectins and the like or other molecules such as DNA, hormones and the like. Therefore, the method of derivatization of acrylic microbeads is tedious and availability is limited. Monomeric glutaraldehyde has been used as a biochemical reagent to covalently bond proteins such as immunoglobulins to ferritin polymeric microspheres and other small particles which were then utilized to map receptors on cell membranes. However, the reaction mechanism of proteins with glutaraldehyde is difficult to ascertain since its structure is still not clear and it has been reported to be in equilibrium with cyclic and hydrated forms. The reaction is difficult to carry out and frequently gives unsatisfactory results.

Direct protein bonding polyglutaraldehyde or copolymers therefore disclosed in copending applications Ser. Nos. 21,988, now U.S. Pat. No. 4,267,235, and 21,989, now U.S. Pat. No. 4,267,234, both filed Mar. 19, 1979 prepared by solution polymerization in aqueous basic medium. In contrast to monomeric glutaraldehyde, the polymers contain conjugated aldehyde groups. This imparts stability to the Schiff's bases formed after reaction with proteins and, further, since the hydrophilic polyglutaraldehyde has relatively long chains extending from the surface into the surrounding aqueous medium, the heterogenous reaction with protein in facilitated.

Polyglutaraldehyde (PGL) microspheres can be directly prepared by suspension polymerization with stirring in presence of surfactant or by precipitation from solution containing surfactant. Magnetic, high density or electron dense microspheres can be prepared by coating metal particles or by suspension polymerization of glutaraldehyde in presence of a suspension of finely divided metal or metal oxide. It has been determined that the PGL microspheres exhibit some degree of non-specific binding to cells. Moreover, though some cross-linking occurs during the homopolymerization of glutaraldehyde, the polymer can be dissolved in highly polar solvents.

A process for polymerizing unsaturated aldehydes such as acrolein is disclosed in U.S. Pat. No. 3,105,801. The process comprises adding a small amount of acid or an acid-acting material to an aqueous solution containing acrolein or other unsaturated aldehyde and exposing the acidic medium to high energy ionizing radiation to form high molecular weight polymer in the form of light powders having non-uniform shapes and sizes. The polymers were not utilized as such but are dissolved in aqueous alkaline sulfur dioxide solution to form water soluble derivatives which are used as coatings or sizings for paper, cloth, fibers and the like. Bell et al also discusses the copolymerization of acrolein with a wide variety of ethylenically unsaturated monomers such as ethylene diamine, pyridine or acrylic acids or esters, vinyl halides, etc. in amounts from 0.1 to 60%, preferably from 1% to 25% by weight of the monomer mixture.

The monomer mixture can contain other agents such as stabilizing, suspending as emulsifying agents. Radiation accelerators such as halides or metal salts may be added to the reaction mixture.

Though the polyacroleins prepared by Bell et al have a high degree of available aldehyde function, there was no recognition of the use of such material as a biological reagent. Furthermore, the presence of extraneous ingredients interfaces with the purity of the polymer and it would not be suitable as a biochemical protein bonding agent. Specific modification of the material by copolymerization with certain comonomers designed to impart further properties such as nonspecific binding and modification to add other functional groups for introduction of dyes, proteins or other materials which would improve the flexibility of use of the material is disclosed in concurrently filed copending application Ser. No. 248,899 filed Mar. 30, 1981 entitled "Polyacrolein Microspheres", the disclosure of which is expressly incorporated herein by reference.

DESCRIPTION OF THE INVENTION

It has now been disclosed in accordance with the invention that aldehyde substituted microspheres can be formed in situ and grafted onto diverse, inert substrates such as polymeric films, rods, tubes, particles or spheres to form a hybrid coated material. The hybrid material efficiently binds aldehyde reactive organic molecules and proteins. The method converts inert materials into functionally reactive, direct protein bonding materials. The surface area of the substrate is increased due to the coating of covalently bonded submicron sized microspheres. The coated article such as a sheet or a continuous band of microsphere coated resin or elastomer provides an efficient system for contacting fluids containing the substance to be separated or bound.

The size and functionality of the microspheres can be controlled by selection of polymerization conditions and selection of functionally substituted copolymerizable monomers. The functional nature of the microspheres can be modified by post-polymerization coupling reactions.

The hybrid product is produced in accordance with the invention by forming a dilute solution of addition polymerizable unsaturated aldehyde, placing the inert substrate in the solution and applying high energy radiation to the solution. The radiation initiates polymerization of the aldehyde which forms microspheres which attach to the substrate. Rosette appearing products are formed when spherical polymeric substrates are utilized. Polymerization in the presence of surfactants results in formation and attachment to the surface of more uniformly shaped and smaller microspheres.

Adding a solvent to the polymerization that is a nonsolvent for the microspheres but is a solvent for the surface of the substrate causes swelling of the surface and a firmer attachment of the microsphere layer. The layer of microspheres appears to be transparent. However, the layer can be rendered fluorescent by interpolymerization with additional polymerizable or aldehyde reactive monomers. Electron dense or magnetizable metals can be incorporated into the microspheres during polymerization.

The invention provides a method of immobilizing high concentrations of enzymes, proteins, hormones, viruses, cells and varied other organic and biological molecules on the surface of inert commercial plastics. The coated substrates can be used in separation techniques, clinical diagnostic tests, battery separators and as biological and chemical catalyst supports.

The microsphere coated products of the invention exhibit little or no aggregation during or after derivatization reaction to introduce large amounts of antibodies or other proteins, fluorochromes, etc. The microsphere film is insoluble, has functional groups directly reactive with protein, which can bind specifically to receptor sites on cells and the individual microspheres can readily be prepared in sizes from 100 Angstroms to 2,000 Angstroms, or up to 10 microns or larger if desired.

The derivatization procedure is simplified. Hydroxyl modified microspheres can be used to chelate metals as a purification media or as a support for a catalyst. The microspheres of the invention provide a reliable, simple method to label cells for research, analysis or diagnosis.

The microsphere coated products of the invention can also be utilized as a substrate to bind pharmaceuticals containing functional groups reactive with aldehyde or with the hydrophillic hydroxyl, carboxyl or amine substituent or with the functional group Z of the adduct. The microsphere-pharmaceutical adduct is less likely to migrate and should reduce side effects. Furthermore, antibodies can be attached to the microsphere coated product so that it migrates to specific cells having corresponding antigen receptor sites. Magnetically attractable microsphere coated products can be accumulated at a specific location in a subject by application of a magnetic field to that location.

These and many other features and attendant advantages of the invention will become apparent as the invention becomes better understood by reference to the following detailed description when considered in conjunction with the accompanying drawings.

DESCRIPTION OF THE INVENTION

Figure 1:
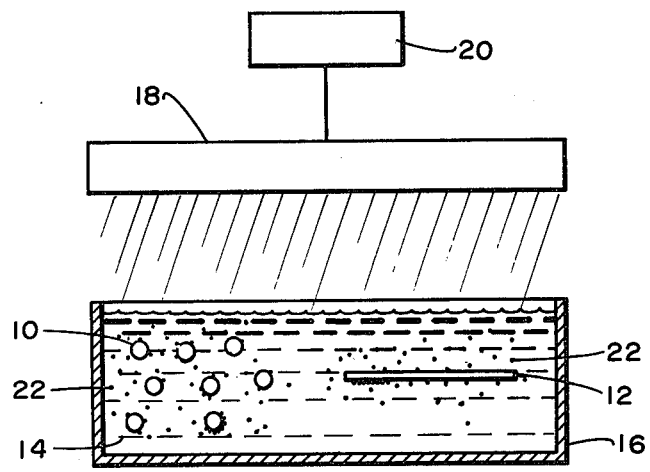
FIG. 1 is a schematic view of the apparatus for forming a microsphere coated product of the invention.
Figure 2:
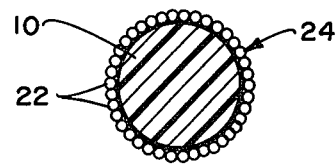
FIG. 2 is a cross-sectional view of a microsphere coated bead in accordance with the invention.
Figure 3:
FIG. 3 is a side view of a microsphere coated sheet.

Referring now to FIGS. 1 to 3, the microsphere coated articles are formed by disposing a substrate such as a plastic sphere 10 or plastic sheet 12 in a solution 14 of unsaturated aldehyde contained in a reaction tank 16. Radiation source 18 powered by power supply 20 is turned on and microspheres 22 and formed in solution, migrate to the surface of spheres 10 and sheet 12 and are grafted thereto form a continuous coating or layer 24 of tangential microspheres. The layer on the beads need comprise only a continuous monolayer of microspheres in order to provide the desired functionality. The layer is applied in a very even, uniform manner and generally is present in an amount from 100 Angstroms to 1,000 microns, generally from 500 Angstroms to 100 microns in thickness. The microspheres are produced by addition polymerization of a liquid polymerization system optionally including a dispersion of metal particles. More uniformly sized and shaped beads are formed in very dilute aqueous monomer mixtures of no more than 20% by weight, preferably 1 to 10% by weight of dissolved monomers. Surfactants may be present to aid in the dispersion of the metal particles and form smaller microspheres.

The polymerization proceeds with or without stirring with application of high energy radiation capable of generating free radicals in the aqueous system. The radiation source is suitably a cobalt 60 gamma source or cesium source and doses of 0.05 to 2.0 megarads are sufficient for polymerization. The reaction is preferably conducted under oxygen excluding condition, generally by applying vacuum to the reaction vessel or by displacing oxygen gas from the system with an inert gas such as nitrogen.

The addition of 0.05 to 5%, by weight, of a stabilizing agent to the aqueous polymerization system before polymerization is found to prevent agglomeration of individual microspheres before they attach to the surface of the substrate. The stabilizing agent is suitably a non-ionic material such as an aqueous soluble polymer such as a polyalkylene oxide polyether or nonionic surfactants. Representative non-ionic surfactants are Tweens which are polyoxyethylene derivatives of fatty acid partial esters of sorbitol, Triton X, or dextrans. The polyethers generally have a molecular weight from 10,000 to 10,000,000, preferably 400,000 to 6,000,000 and are polymers of ethylene oxide, propylene oxide or their mixtures. Polyethylene oxides (PEO) and Triton X are preferred, non-ionic agents.

Smaller microspheres (50 to 200 Angstroms in diameter) are formed in solutions containing small amounts, typically from 10 to 150 millimoles, of an anionic surfactant such as an alkali metal $C_8$ to $C_{20}$ alkyl sulfate surfactant such as sodium lauryl sulfate (SLS) or sodium dodecyl sulfate (SDS).

The ethylenically unsaturated aldehyde should comprise at least 10% by weight of the monomer mixture preferably from 20% to 90% by weight thereof. The aldehydes preferably have the ethylenic group in alphabeta position relative to the aldehyde group and can be selected from those aldehydes containing up to 20 carbon atoms such as acrolein, methacrolein, alpha-ethyl acrolein, alpha-butylacrolein, alpha-chloroacrolein, beta-phenylacrolein, alpha-cyclohexyl acrolein and alpha-decylacrolein. Preferred aldehydes contain 4 to 10 carbon atoms and especially acrolein and $C_1$ to $C_8$ aryl alkyl and cycloalkyl substituted derivatives thereof.

Presence of mono-unsaturated covalent-bonding monomers containing functional hydrophilic groups such as amine, carboxyl or hydroxyl provides non-specific binding and provides further functional groups for introduction of proteins, dyes and the like. The comonomers are freely water soluble and can comprise from 10 to 50% of the monomer mixture. These monomers are suitably selected from amino, carboxyl or hydroxyl substituted acrylic monomers. Exemplary monomers are acrylamide (AM), methacrylamide (MAM), acrylic acid, methacrylic acid (MA), dimethylaminomethacrylate or hydroxyl-lower alkyl or amino-lower-alkyl-acrylates such as those of the formula:

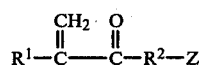

where $R^1$ is hydrogen or lower alkyl of 1-8 carbon atoms, $R^2$ is alkylene of 1-12 carbon atoms, and Z is —OH or $R^3$—N—$R^4$ where $R^3$ or $R^4$ are individually selected from H, lower alkyl or lower alkoxy of 1-8 carbon atoms. 2-hydroxyethyl methacrylate (HEMA), 3-hydroxypropyl methacrylate and 2-aminoethyl methacrylate are readily available commercially. Porosity and hydrophilicity increase with increasing concentration of monomer.

Though apparently the radiation provides cross-linking of the polymer, further cross-linking can be provided by inclusion of polyunsaturated compounds which are generally present in the monomer mixture in an amount from 0.1-20% by weight, generally 6-12% by weight and are suitably a compatible diene or triene polyvinyl compound capable of addition polymerization with the covalent bonding monomer such as ethylene glycol dimethacrylate, trimethylol-propane-trimethacrylate, N,N'-methylene-bisacrylamide (BAM), hexahydro-1,3,5-triacryloyl-s-triazine or divinyl benzene.

For small particle size and additional reduction in non-specific binding and agglomeration the monomer mixture preferably contains a monomer capable of imparting negative charge such as methacrylic acid (MA). The mixture may contain 0-40% suitably 10 to 30% of sparingly water soluble monomers having hydrophobic characteristics since this is found to result in freely-suspended, individual, small microspheres. The cross-linking agent is sometimes sparingly water soluble. Hydrophobic characteristics can also be provided with monomers such as lower alkyl acrylates suitably methyl methacrylate or ethyl methacrylate or a vinyl pyridine. Vinyl pyridines suitable for use in the invention are 2-vinyl pyridine, 4-vinyl pyridine and 2-methyl-5-vinyl pyridine.

Small microspheres containing electron-dense metals provide higher spatial resolution of cell surface features. Immunomicrospheres containing electron-dense metals provide more stable labels than gold particles with physically absorbed antibodies that are presently used for call labeling. The metal containing microspheres can be synthesized by, in situ, polymerization of the microspheres in presence of a suspension of finely-divided metal particles or compounds of the metal, preferably a colloidal dispersion of the metal. The metal is incorporated into the microsphere in an effective amount of from 0.5% to 40% by weight, generally from 5% to 25% by weight.

The metal or metal compound particles are preferably fine, evenly sized materials having a uniform diameter smaller than the resultant microsphere diameter, typically below 1000 Å, generally from 25 Å to 500 Å. The metals are preferably the electron-dense heavy metals having a high atomic number above 50, preferably above 75 such as Pb, Ni, Co, Pt, Au, Fe. The metal may be magnetically attractable such as Fe, Ni, Co or alloys thereof or an inorganic magnetic compound such as a metal oxide. The magnetic material is preferably a magnetic iron oxide of the formula $Fe_3O_4$. Some hard, ceramic type ferrites, such as lithium ferrites can also be used. The metal or compound can be made into a readily dispersible form by suspension in water containing a surfactant such as polyethylene imine.

Post polymerization reaction with specific fluorocrome reagents that are not in themselves fluorescent, results in a fluorescent microsphere by forming fluorescent chromophores attached to the polymer. Anthrone reacts with acrolein units to form a benzanthrone fluorogen and m-aminophenol reacts with the acrolein structure to form the fluorogen, 7-hydroxyquinoline. Aminofluorescein also reacts with aldehyde groups to form fluorescent microspheres.

The microspheres can also be rendered fluorescent during polymerization in presence of fluorochrome compounds containing aldehyde or hydroxyl reactive groups such as aminofluorescein, 9-amino acridine, propidium bromide or fluorescein isothiocyanate (FITC). Highly fluorescent microspheres can also be prepared by suspension polymerization in presence of fluorochromes containing unsaturated groups capable of reaction with acrolein.

Another manner of introducing functionality other than aldehyde onto the microsphere layer is by adduct reaction of the microspheres with compounds of the formula:

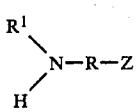

where $R^1$ is hydrogen or a hydrocarbon group which may be aliphatic or aromatic preferably aryl such as phenyl or alkyl or 1 to 10 carbon atoms, R is a divalent hydrocarbon group such as alkylene of 1 to 20 carbon atoms and Z is a functional group such as amine or hydroxyl or RZ can be hydroxyl. Representative compounds are hydroxylamine or ethylene diamine. The microsphere layer can be modified to introduce carboxyl groups by oxidation with an agent such as hydrogen peroxide.

The substrate can be of diverse physical or chemical nature. The substrate must be capable of withstanding the high energy radiation without deterioration. Though the microsphere layer would probably form on metal, ceramic or glass or plant material substrates such as wood, the preferred substrates are synthetic organic resin materials capable of developing covalent bonds during high energy radiation.

The resin can be hydrocarbon such as polyethylene polypropylene, polystyrene or polyester, polyamide, dextran acrylic polymers such as polyacrylamide, polyacrylate, etc. Though functional groups reactive with aldehyde are not necessary, they would contribute to forming a further means of bonding the microsphere layer to the substrate. The substrate should be at least ten times larger than the microsphere and can be in the form of a sheet, rod, tube, sphere, hollow sphere, irregular particle, etc.

Examples of practice follow: Reagents: Methacrylic acid (MA), 2-hydroxyethyl methacrylate (HEMA), acrolein, ethylene diamine were fractionally distilled. Polyethylene oxide (PEO, $M_w$ 100,000) N,N'-methylene-bis-acrylamide (BAM), hydroxylamine hydrochloride, 1,6-hexane diamine, l.Lysine, 1-ethyl-3-(3-dimethyl amino propyl) carbodiimide and sodium dodecyl sulfate (SDS) were used as received.

Procedure: Acrolein or monomer mixtures consisting of HEMA and acrolein or HEMA, BAM, MA and acrolein formed homogeneous solutions in distilled water containing PEO or SDS. The polymer substrates were added to the solution. After dearation with nitrogen the mixtures were irradiated in CO gamma source at room temperature (dose rate 0.12 Mr/hour) for various periods. The reaction product was purified and kept in distilled water.

Methods: The aldehyde content was determined from the percent nitrogen of the oxime prepared by the reaction of an aqueous suspension with hydroxylamine hydrochloride [P. J. Bochert Kunstoffe 51 (3) 137 (1961)].

IR spectra were obtained with a Fourrier transform IR (fts-15C, Houston Instruments) spectrophotometer.

EXAMPLE 1

Polypropylene sheets were placed in a 10% (v/v) acrolein solution in water and irradiated for 0,20,40,60 and 120 minutes. The irradiated sheets were examined by SEM. There was no coating on the non-irradiated sheet. However, the irradiated sheet showed progressively more attachment of microspheres with irradiation time. Control sheets irradiated in water alone do not exhibit any microspheres on their surface.

EXAMPLE 2

Sheets of polymethylmethacrylate were run according to the conditions of Example 1. The results were similar except that the attachment of microspheres was visible without microscope.

EXAMPLE 3

Polypropylene sheets were placed in aqueous solutions each containing 0.4% by weight PEO and containing respectively; 10%, 8%, 5%, 2% and 0% acrolein. Each solution was exposed to irradiation for 90 minutes and each sheet was stained with Geimsa strain and 9-aminoacridine fluorescent dye. The non-irradiated (10% acrolein) sheet and the 0% acrolein sheet did not react with the stain. However, all other sheets exhibited fluorescence.

EXAMPLE 4

Example 3 was repeated with polystyrene sheets. The sheets were treated overnight with 9-aminoacridine. Again the non-irradiated (10% acrolein) and 0% acrolein sheets did not exhibit fluorescence. However, some fluorescent microspheres were visible on the surface without aid of microscope and under 1000× magnification, an even coating of fluorescent microspheres was observed.

EXAMPLE 5

Polypropylene sheets were immersed in an aqueous solution containing 5% acrolein and containing 0%, 0.5% 2%, and 5% of SDS. Each solution and control sheet in a 0% acrolein solution were irradiated for 90 minutes. These sheets and a control sheet dipped into the 5% acrolein solution were stained with 9-aminoacridine. The irradiated sheet did not fluoresce. The sheet from the solution not containing SDS exhibited fluorescent beads. The sheets treated with SDS solutions were fluorescent but individual beads could not be observed.

EXAMPLE 6

Polystyrene sheets were subjected to the conditions of Example 5 with similar results.

EXAMPLE 7

One ml of Styrene-divinyl benzene (S/DVB) beads (8 microns); suspension (0.14 g/ml) containing 0.4% PEO and 5% acrolein, were irradiated in a cobalt gamma source for 0, 20, 40, 60 and 90 minutes. Polyacrolein (PA) microspheres formed in the suspension and attached to the surface of the beads to form hybrid beads. (PA-PS) The PA microspheres were separated from the hybrid beads by sedimentation; washing once with PEO and 3× with water.

When the recovered beads were reacted 1 M hydroxylamine hydrochloride for 4 hours, the non-irradiated beads remained white while the 20–90 minute irradiate beads turned yellow indicating shift base formation.

When the recovered beads from the 0 and 90 minute irradiated beads were subjected to reaction with 9-aminoacridine, the non-irradiated beads are non-fluorescent while the radiated beads were fluorescent. The same results were observed on treatment with 0.05 ml of 20 mg/ml suspension of fluorescent goat antirabbit antibodies (GAR). When the 90 minute irradiated, rosette-shaped hybrid spheres were reacted with sheep red blood cells (RBC) sensitized with RAS Ig; an adduct was formed.

EXAMPLE 8

The PS/DVB bead suspension of Example 7 containing 2 mg/ml of SDS was irradiated for 3 hours and then washed in water. SEM photographs showed small PA microspheres on irradiated PS bead surface and no PA on the non-irradiated control.

EXAMPLE 9

Sephadex 6-10 (dextran) beads were irradiated for 2 hours in 5% acrolein solution containing 0.4% PEO. The irradiated beads and non-irradiated control were reacted with 0.05 ml of a 20 mg/ml fluorescent goat antirabbit—Ig for 2 hours. Irradiated beads exhibited fluorescent coating which can not be washed off with pH 2.2, 0.2 M glycine wash. The control was non-fluorescent.

EXAMPLE 10

Biorad Biogel G-30 (polyacrylamide) beads were treated according to the procedure of Example 9 with the same results.

EXAMPLE 11

Bis-acrylamide-acrylamide—hydroxyethylmethacrylate beads (42 mg) were irradiated for one hour in 20% acrolein aqueous solution containing 0.4% PEO. The non-irradiated control did not form any coating. The rosette-shaped hybrid beads (6.5 mg) resulting from the irradiated procedure were coated with GAR (1.7 mg) and the Ig-bead adduct was added to 10%/ml of sheep RBC sensitized with RAS Ig.

A new convenient immunoreagent in form of acrolein hybrid microspheres was synthesized in a variety of sizes. High intensity of fluorescence can be imparted to the microspheres during or after polymerization. The aldehyde functional groups permit covalent bonding with antibodies, enzymes and other proteins in a single step. Therefore this immunoreagent eliminates the previously used intermediate steps in which the cyanogen bromide and carbodiimide reaction was used. The high specificity of the microspheres, at least as far as human rbc is concerned is also a desirable property. A minor synthetic modification yields fluorescent, magnetic microspheres for a large number of potential applications. The polyacrolein hybrid microspheres of this invention contain more aldehyde groups than the comparable glutaraldehyde copolymer microspheres.

The use of magnetic particles has created a great deal of interest in biochemical research and clinical medicine when used as supports for immobilized enzymes. Their easy retrieval from liquors containing colloids and undissolved solids should be of practical value. The separation of proteins and chemical compounds by affinity chromatography can be simplified by elimination of tedious centrifugation procedures and column chromatography steps. Magnetic particles have also recently been tested in radioimmunoassay techniques in hyperthermia treatment of cancer, in guidance of magnetic particles to a vascular malformation such as cerebral aneurism with the intent to seal the defect by inducing thrombosis.

Other proposed applications have been as tracers of blood flow or vehicles for drug delivery. The first successful application of magnetic immunomicrospheres to the separation of B and T cells has been demonstrated. There is little doubt that physical sorting of cell subpopulations has become a necessity. Many separation methods, while useful are limited by the restricted set of parameters upon which separation can be based and by the fact that they are batch techniques.

New flow cytometers and sorters permit quantitative multiparameter measurements and sorting based on these measurements, but are limited as far as the number of cells that can be separated in a given time. Magnetic cell sorters have the potential of cell separation in a continuous process. Evidence obtained using model cell systems indicates that magnetic immunomicrospheres of desirable sizes can be conjugated with proteins in a simple and convenient manner, therefore offer a potential for large scale immunological cell sorting as well as other applications.

It is to be understood that only preferred embodiments of the invention have been described and that numerous substituents, midifications and alterations are permissible without departing from the spirit and scope of the invention as defined in the following claims.

We claim:

1. A coated article comprising:
   a synthetic organic resin substrate, said resin being capable of developing covalent bonds during high energy radiation;
   a continuous layer of contiguous, tangential, individual microspheres having an uniform diameter between 100 Angstroms and 2000 Angstroms bound to the surface of the substrate by covalent bonds formed between the resin and the microspheres by means of high energy radiation grafting of the microspheres to the surface of the resin substrate, said microspheres consisting essentially of the addition polymerized polymer of an unsaturated aldehyde containing 4 to 20 carbon atoms.

2. A coated article according to claim 1 in which the resin is selected from polyethylene, polypropylene, polystyrene, acrylic polymers or dextran.

3. A coated article according to claim 1 in which the polymer further consists essentially of at least 20% of an addition polymerizable comonomer having a hydrophilic substituent selected from hydroxyl, amino or carboxyl.

4. A coated article according to claim 1 in which the substrate is at least 10 times larger than the microspheres.

5. A coated article according to claim 4 in which the thickness of the layer is from 100 Angstroms to 1000 microns.

6. An article according to claim 4 in which the substrate is in the form of spheres, particles, sheets, rods or tubes.

7. An article according to claim 6 in which the aldehyde is selected from acrolein and $C_1$ to $C_8$ alkyl, aryl and cycloalkyl derivatives thereof.

8. A composition comprising an adduct of the article of claim 1 with a material selected from aldehyde reactive proteins, pharmaceuticals and fluorescent chromophores.

9. A composition according to claim 8 in which the aldehyde is acrolein.

* * * * *

UNITED STATES PATENT AND TRADEMARK OFFICE
CERTIFICATE OF CORRECTION

PATENT NO. : 4,438,239
DATED : March 20, 1984
INVENTOR(S) : Alan Rembaum and Richard C. K. Yen It is certified that error appears in the above-identified patent and that said Letters Patent are hereby corrected as shown below:

Column 3, line 10, change "interfaces" to --interferes--

Column 4, line 24, correct spelling of "hydrophilic"
         line 55, after "thereto" add --to--

Column 6, line 37, change "call" to --cell--
         line 61, correct spelling of "fluorochrome"

Column 7, line 60, change "dearation" to --deaeration--
         line 68, "51" should be underscored Column 8, line 1, change "Fourrier" to --Fourier--
         line 26, change "strain" to --stain--

Column 10, line 26, change "substituents" to --substitutions--
          line 26, change "midifications" to --modifications--

Signed and Sealed this

Twenty-sixth Day of June 1984

[SEAL]

Attest:

GERALD J. MOSSINGHOFF

Attesting Officer      Commissioner of Patents and Trademarks